(12) United States Patent
Bopp et al.

(10) Patent No.: US 7,399,628 B2
(45) Date of Patent: Jul. 15, 2008

(54) BODY FOR FLOW-THROUGH CELLS AND THE USE THEREOF

(75) Inventors: Martin Andreas Bopp, Basel (CH); Heinrich Büttgen, Bad Krozingen (DE); Tilo Callenbach, Jona (CH); Werner Schoch, Dübendorf (CH); Yves Marmier, La Chaux-de Fonds (CH); André Marcel Wicky, Cudrefin (CH)

(73) Assignee: Bayer Technology Services GmbH, Leverkusen (DE)

( * ) Notice: Subject to any disclaimer, the term of this patent is extended or adjusted under 35 U.S.C. 154(b) by 0 days.

(21) Appl. No.: 10/480,423

(22) PCT Filed: Jun. 10, 2002

(86) PCT No.: PCT/CH02/00309

§ 371 (c)(1),
(2), (4) Date: Dec. 12, 2003

(87) PCT Pub. No.: WO02/103331

PCT Pub. Date: Dec. 27, 2002

(65) Prior Publication Data

US 2004/0185576 A1    Sep. 23, 2004

(30) Foreign Application Priority Data

Jun. 15, 2001 (CH) .................................. 1089/01

(51) Int. Cl.
*C12M 1/34* (2006.01)

(52) U.S. Cl. ............... 435/288.4; 422/50; 422/52; 422/55; 422/58; 422/82.11; 422/82.05; 422/68.1; 435/288.3; 435/288.7

(58) Field of Classification Search ............... 422/50, 422/52, 55, 58, 68.1, 82.11, 82.05; 435/4, 435/7.1, 283.1, 287.1, 288.3, 288.4, 288.5, 435/288.7; 436/43, 52
See application file for complete search history.

(56) References Cited

U.S. PATENT DOCUMENTS 3,884,072 A * 5/1975 Cheng .................... 73/215

(Continued)

FOREIGN PATENT DOCUMENTS

EP    1 072 881    1/2001

(Continued)

OTHER PUBLICATIONS

Petrou et al., Microdevice with integrated dialysis probe and biosensor array for continuous multi-analyte monitoring, May 2003, Biosensors and Bioelectronics, vol. 18, pp. 613-619.*

*Primary Examiner*—Long V. Le
*Assistant Examiner*—Melanie J Yu
(74) *Attorney, Agent, or Firm*—Wenderoth, Lind & Ponack, L.L.P.

(57) ABSTRACT

A system of flow-through cells is obtained by assembling a body with a base plate. The body has a first spring element and a first stop, disposed on opposite end sections of the body, at least one second spring element and a corresponding second stop, disposed on opposite faces of the body, and at least one support element and at least one retaining element, which are adapted for the exact positioning of the body in the receiving openings of a support in three directions.

19 Claims, 11 Drawing Sheets

U.S. PATENT DOCUMENTS

| | | | | |
|---|---|---|---|---|
| 5,019,351 | A * | 5/1991 | Schulz | 422/99 |
| 5,571,410 | A * | 11/1996 | Swedberg et al. | 210/198.2 |
| 5,650,125 | A | 7/1997 | Bosanquet | |
| 5,958,782 | A * | 9/1999 | Bentsen et al. | 436/79 |
| 6,078,705 | A | 6/2000 | Neuschäfer et al. | |
| 6,108,463 | A * | 8/2000 | Herron et al. | 385/12 |
| 6,137,117 | A * | 10/2000 | Feldstein et al. | 250/573 |
| 6,159,739 | A * | 12/2000 | Weigl et al. | 436/52 |
| 6,192,168 | B1 * | 2/2001 | Feldstein et al. | 385/12 |
| 6,198,869 | B1 * | 3/2001 | Kraus et al. | 385/129 |
| 6,300,141 | B1 * | 10/2001 | Segal et al. | 435/287.1 |
| 6,384,912 | B2 * | 5/2002 | Kraus et al. | 356/246 |
| 6,653,136 | B1 * | 11/2003 | Dodgson et al. | 435/461 |
| 6,811,752 | B2 * | 11/2004 | Barbera-Guillem | 422/100 |
| 6,825,047 | B1 * | 11/2004 | Woudenberg et al. | 436/518 |
| 6,951,632 | B2 * | 10/2005 | Unger et al. | 422/100 |
| 2002/0182631 | A1 * | 12/2002 | Schurmann-Mader et al. | 435/6 |
| 2003/0017077 | A1 * | 1/2003 | Hahn et al. | 422/81 |

FOREIGN PATENT DOCUMENTS

| | | |
|---|---|---|
| WO | 00/03805 | 1/2000 |
| WO | 01/43875 | 6/2001 |

* cited by examiner

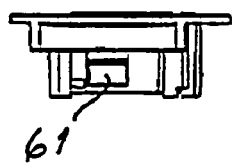 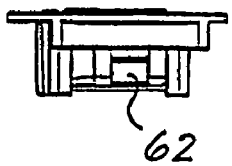
Fig. 4      Fig. 5
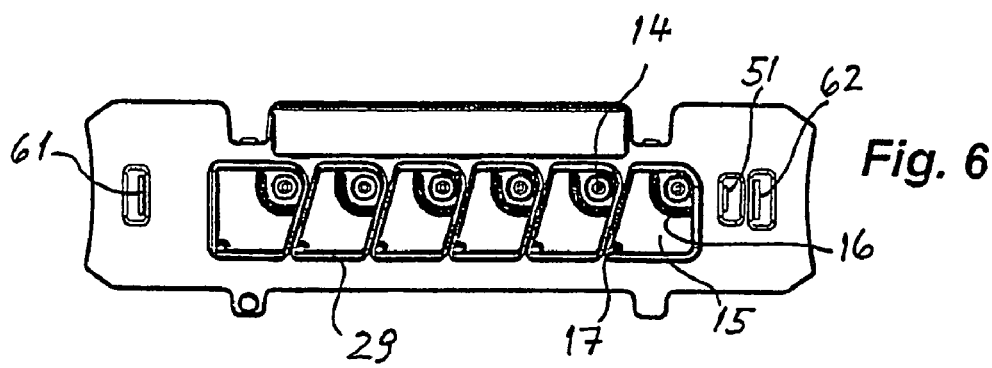
Fig. 6
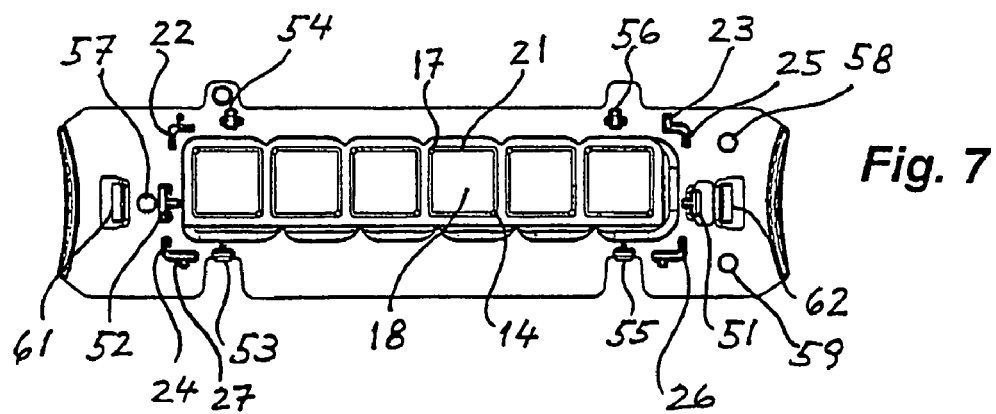
Fig. 7

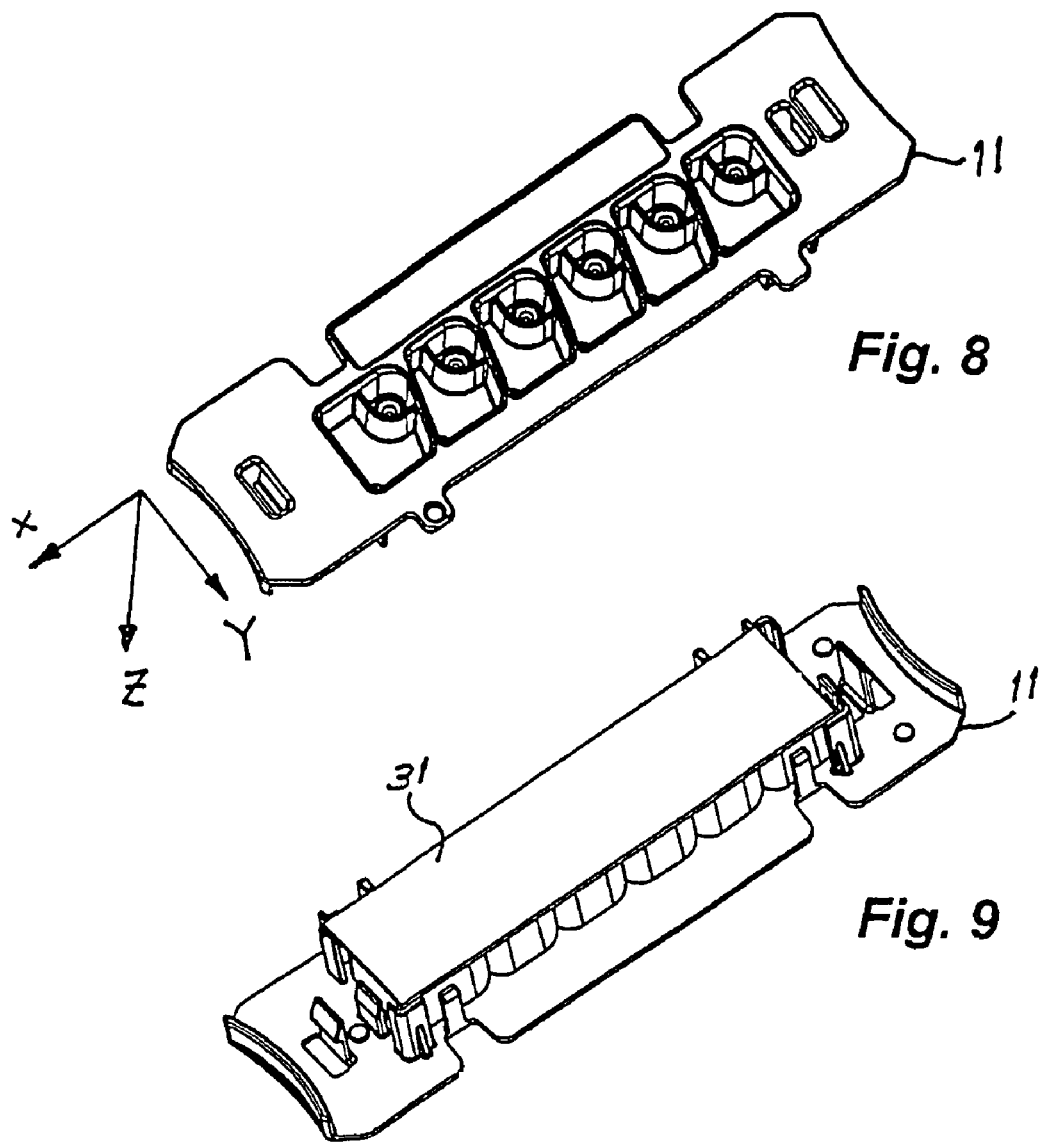
*Fig. 8*
*Fig. 9*
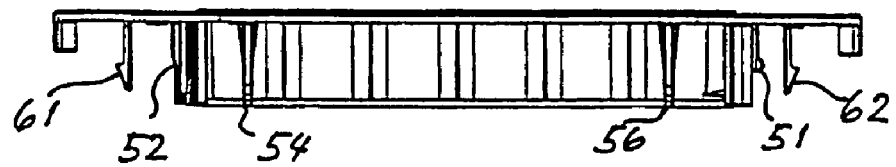
*Fig. 10*

BODY FOR FLOW-THROUGH CELLS AND THE USE THEREOF

BACKGROUND OF THE INVENTION

1. Field of the Invention

The invention relates to a body for the formation of an arrangement of flow-through cells.

The invention relates further to a carrier and the arrangement of flow-through cells.

2. Description of the Related Art

An arrangement of flow-through cells of the above-mentioned type is described in international patent application PCT/EP 00/12668 cited hereinbelow.

FIGS. 24-28 show embodiments which are described in international patent application PCT/EP 00/12668.

FIG. 24 is identical to FIG. 1 of patent application PCT/EP 00/12668 and shows a partial view of a first arrangement of flow-through cells in cross-section. This figure shows an inlet 1 and an outlet 2 of an individual flow-through cell, as well as parts of the adjacent flow-through cells.

The flow-through cell arrangement shown in FIG. 24 comprises a base plate 4 and a fitted body 6. The body 6 features a recess 3, which after connection of the body 6 to the base plate 4 forms a space for creating a flow-through cell with the inlet 1 and the outlet 2. The recess 3 may have any basic surface area; for example, it may be rectangular. Corners are preferably rounded. The outlet 2 and the inlet 1 of the adjacent flow-through cells in the cross-sectional direction are likewise shown. The inlet and outlet of a flow-through cell are preferably each arranged at opposite end-points of the base areas of the recess, for example, at the end-points of the diagonal in the case of an essentially rectangular base area.

FIG. 25 is identical to FIG. 2 of patent application PCT/EP 00/12668 and shows in cross-section a partial view of another embodiment of the flow-through cell arrangement according to FIG. 24. In the embodiment according to FIG. 25, a reservoir 5 is formed as a well in the outer wall of the body 6 connected with the base plate 4. This embodiment enables liquid from the flow-through cell to enter the reservoir 5, but not to flow back into the flow-through cell as long as the reservoir 5 is not filled to the upper edge of the rim on the liquid outlet side.

FIG. 26 is identical to FIG. 3 of patent application PCT/EP 00/12668 and shows in cross-section a partial view of a further embodiment of the flow-through cell arrangement according to FIG. 24. In the embodiment according to FIG. 26, the reservoir 5 is closed off at the top. The result of this embodiment is that also no liquid can escape from the reservoir 5 by evaporation.

In all the above-mentioned embodiments, the body 6 may consist of one part or also of several parts which are preferably joined irreversibly into a unit.

FIG. 27 is identical to FIG. 4 of patent application PCT/EP 00/12668 and shows a cross-sectional partial view essentially confined to the base plate for an embodiment featuring an optical film waveguide as the base plate. In the embodiment according to FIG. 27, the base plate is provided as an optical film waveguide with biological, biochemical or synthetic recognition elements immobilized thereon. According to FIG. 27, this film waveguide comprises layers a, b and b'. The reference symbol g is used in FIG. 27 to indicate the limitations of a flow-through cell which is created by connecting the base plate with the body 6. Reference symbol g thus corresponds to the reference symbol 6 in FIGS. 24 to 26.

On the layer b which is transparent at least in part of the visible or near-infrared spectrum, the thin intermediate layer b' is first applied and then the layer a, whose refractive index is greater than the refractive indices of layers b and b'. Also, layers a and b' are optically transparent at least in part of the visible or near-infrared spectrum. In the layer b, grating structures c and c' are formed as relief gratings, which on application of the layers above these gratings are transferred to these layers. On the layer a, an adhesion-promoting layer f is applied which can improve the adhesion of biological, biochemical or synthetic recognition elements to be immobilized. In this embodiment, these recognition elements are immobilized in spatially separated measurement areas d, which in this embodiment are arranged both on and between the grating structures c and c'. In this embodiment according to FIG. 27, the base plate is finally connected with the body g, which corresponds to the body 6 in FIGS. 24 to 26.

FIG. 28 is identical to FIG. 5 of patent application PCT/EP 00/12668 and shows an arrangement of flow-through cells in which column-shaped arrangements of base plates 4 and the connected bodies 6 together form application blocks 7, which are set in corresponding receiving openings of a common carrier 8 (meta-carrier). In this way, an arrangement of a total of 6 columns each of 6 flow-through cells is created. In the embodiment according to FIG. 28 the carrier has the basic dimensions of a standard microtiter plate. Inlet openings 9 to the inlets 1 (not visible in this figure) are positioned in such a way that they are compatible with the pitch of a standard 96-well microtiter plate, i.e., they are positioned at intervals in each case of an integral multiple of 9 mm (for example: interval of inlets within a column: 9 mm; interval of inlets between adjacent columns: 18 mm). With a corresponding translation of the carrier with the application blocks, the reservoirs 5 are compatible with the pitch of a standard 96-well microtiter plate. In the embodiment, according to FIG. 28, the carrier 8 is designed in such a way that it can take up to 6 blocks. However, spaces for application blocks may also remain unoccupied.

SUMMARY OF THE INVENTION

A very exact positioning of the flow-through cell arrangement in a carrier is indispensable to ensure the reliability and precision of the measurements conducted, for example, optical, electro-optical or electrical measurements.

The invention is therefore based on the objective of providing a flow-through cell arrangement which is so designed that it can be positioned with a high degree of precision in a carrier which is inserted in an analytical instrument, is in turn positionable here with a high degree of precision and is processed automatically, wherein the processing comprises the performance of measurements, for example, optical, electro-optical or electrical measurements, on a relatively large number of very small measurement areas which lie closely adjacent to each other.

The invention is further based on the objective of providing a body for the formation of a flow-through cell arrangement which:

allows the use of standard, commercially available pipette tips for applying samples or reagents to the cells, and requires smaller volumes of samples and reagents.

According to a first aspect of the invention, the first-named objective is solved with a body.

According to a second aspect of the invention, the first-named objective is solved with a flow-through cell arrangement.

According to a third aspect of the invention, the first-named objective is solved with a carrier.

According to a fourth aspect of the invention, the first-named objective is solved with a flow-through cell arrangement.

According to a fifth aspect of the invention, the first-named objective is solved with a flow-through cell arrangement.

According to a sixth aspect of the invention, the second-named objective is solved by a body.

The further claims provide preferred embodiments and the use of a body, a flow-through cell arrangement or a carrier.

The embodiment or arrangement according to the invention enables a high-precision positioning of a flow-through cell arrangement of the type mentioned in the introduction using mechanical positioning aids, wherein the achievable precision of the positioning lies in the order of magnitude of 50 micrometers and surprisingly no adjustments need to be made.

The preferred field of application of the flow-through cell arrangement according to the invention is the simultaneous (parallel) determination of multiple analytes in one or more samples. This may take place by so-called microarrays being accommodated in the sample compartments, with the base plate in an embodiment as a sensor platform.

The flow-through cell arrangement according to the invention can be used in all analytical measurement procedures which are described or mentioned in the above-named patent application PCT/EP 00/12668.

Further advantages of the invention emerge from the description of preferred examples below.

BRIEF DESCRIPTION OF THE DRAWINGS

FIGS. 1 to 7 show various views of an embodiment of a body according to the invention for the formation of a linear row, i.e., a one-dimensional arrangement of flow-through cells.

FIG. 1 shows a view of the body in perspective from above,

FIG. 2 shows the front view according to FIG. 1,

FIG. 3 shows the view from the rear according to FIG. 1,

FIG. 4 shows the view from the left according to FIG. 1,

FIG. 5 shows the view from the right according to FIG. 1,

FIG. 6 shows the view from above according to FIG. 1, and

FIG. 7 shows the view from below according to FIG. 1.

FIGS. 8 to 15 show various views of an embodiment of a flow-through cell arrangement according to the invention which is formed by joining together a body according to FIGS. 1 to 7 and a base plate.

FIG. 8 shows a view of the flow-through cell arrangement in perspective from above, FIG. 9 shows a view of the flow-through cell arrangement in perspective from below, FIG. 10 shows the front view according to FIG. 8, FIG. 11 shows the view from the rear according to FIG. 8, FIG. 12 shows the view from the left according to FIG. 8, FIG. 13 shows the view from the right according to FIG. 8, FIG. 14 shows the view from above according to FIG. 8, FIG. 15 shows the view from below according to FIG. 8.

FIG. 16 shows a view of the carrier in perspective from above,

FIG. 17 shows a view of the carrier in perspective from below,

FIG. 18 shows the front view according to FIG. 16,

FIG. 19 shows the view from the rear according to FIG. 16,

FIG. 20 shows the view from the left according to FIG. 16

FIG. 21 shows the view from the right according to FIG. 16,

FIG. 22 shows the view from above according to FIG. 16, and

FIG. 23 shows the view from below according to FIG. 16.

DETAILED DESCRIPTION OF THE INVENTION

Figure 1:
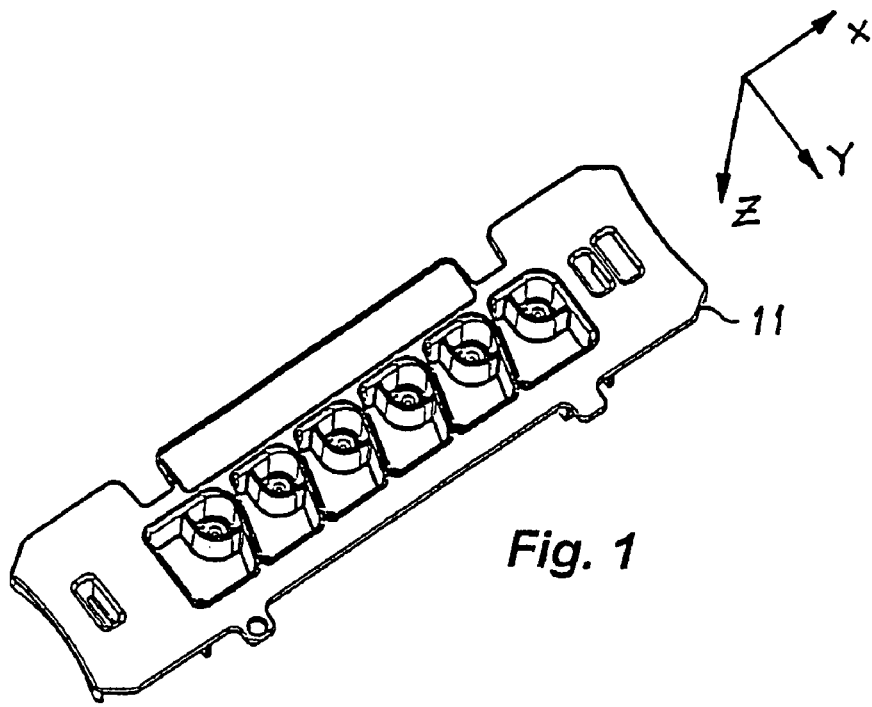

Preferred examples of the invention are described hereinbelow with reference to FIGS. 1-23. They are the result of a further development of embodiments which are described with respect to their basic features in international patent application PCT/EP 00/12668. The content of this patent application is therefore herewith introduced by reference in its entirety as an integral part of the description hereinbelow.

As described in more detail hereinbelow, a one-dimensional or two-dimensional arrangement of flow-through cells serves as the integral part of an array of sample compartments, wherein the arrangement is formed from a base plate and a body connected thereto. An arrangement of recesses is featured corresponding to the arrangement of sample compartments, wherein at least one inlet and one outlet is provided for each sample compartment, and wherein the base plate may, for example, be a glass plate, a waveguide plate or a sensor platform.

In a preferred embodiment, the one-dimensional or two-dimensional arrangement of flow-through cells also enables very small quantities of sample or reagent to be added to and/or withdrawn from the sample compartments, which may be arranged in a large number on a small surface area, wherein for each sample compartment at least one reservoir is integrated in the arrangement for receiving liquid to be withdrawn from the sample container and a peripheral system of liquid inlets and outlets.

(1) FIRST EXAMPLE OF A BODY FOR THE FORMATION OF A FLOW-THROUGH CELL ARRANGEMENT

A body according to the invention for the formation of a linear row, i.e., a one-dimensional arrangement, of flow-through cells is presented in FIGS. 1-7. Such an arrangement of flow-through cells (shown in FIGS. 8-15) is formed by joining together a body 11 with a base plate 31 (not shown in FIGS. 1-7), which carries, e.g., biological, biochemical or synthetic recognition elements. These recognition elements serve to bind and detect the analytes to be determined in applied samples.

The body 11 has an external form which fits into a receiving opening 42 of a carrier 41 (shown in FIGS. 16-23), i.e., the body 11 has an external form which allows it to be inserted in a receiving opening of the carrier.

The body 11 is provided with the following features, which serve to position the body precisely in the receiving opening of the carrier:

(a) a spring 51 and a stop 52, which serve to position the body precisely in the X-direction and are arranged at opposite end sections of the body 11, (b) two springs 53, 55 and two matching stops 54, 56, which serve to position body 11 precisely in the Y-direction and are arranged on opposite sides of the body 11, wherein the Y-direction is perpendicular to the X-direction, and (c) three points of support 57, 58, 59 and two snap-on hooks 61, 62, wherein these points of support and snap-on hooks together serve to position the body precisely in the Z-direction.

The Z-direction is defined as being perpendicular to the plane which is defined by two axes, namely an axis in the X-direction and an axis in the Y-direction.

The spring 51 is located approximately opposite the stop 52.

The spring 53 (and 55, respectively) is located approximately opposite to the stop 54 (and 56, respectively), but slightly offset so that the outer edge of the stop 54 (and 56, respectively) is located in the symmetry plane of the spring 53 (and 55, respectively) parallel to the ZY-plane.

The above-mentioned positioning of elements of the body 11 allow the body 11 and thus the arrangement of flow cells formed therewith to be positioned without any adjustment with an accuracy of +/−50 micrometers in each of the three directions X, Y and Z perpendicular to each other in a receiving opening of the carrier 41 according to FIGS. 16-23.

The snap-on hooks 61 and 62 allow the arrangement to be set in the carrier by gently pressing in the Z-direction and secure the arrangement to prevent it from falling out of the carrier. The arrangement in this case is formed by its outer shape in such a way that an incorrect insertion is mechanically impossible. To remove the arrangement from the carrier, it is sufficient to apply a gentle counterpressure in the Z-direction and thereby slightly press in the snap-on hooks 61 and 62. Alternatively, the snap-on hooks 61 and 62 can also be loosened by applying pressure from below using a suitably designed tool.

Asymmetrically applied mechanical positioning aids in the form of recesses and tabs of the body 11 and the carrier 41, as well as additional circular recesses on one half of the tabs of the body 11 and the carrier 41, serve as optical positioning aids and allow a well-defined positioning of each flow-through cell arrangement in the carrier. A false positioning of the arrangements in the carrier is therefore precluded.

As evident from FIGS. 6 and 7, the pitch of reservoirs 15 which are visible from outside, with the corresponding inlet openings 14, is offset with respect to the pitch of flow-through cells 18 in such a way that inlet openings 14 to the flow-through cells are each located in one of the outer corners thereof.

To facilitate the filling of each flow-through cell 18, the outer surface of the body 11 may feature a wholly or partly circumferential groove 21 for each flow-through cell with a cross-section that has the typical dimensions of between 50×50 micrometers and 500×500 micrometers. Two diagonally opposed corner points of this groove 21 accommodate the inlet opening 14 and outlet opening 17, respectively, of each flow-through cell 18. This groove 21 facilitates the bubble-free filling of the flow-through cell. If the occurrence of air bubbles during the filling process or during the process to be conducted in the flow-through cells for the detection of analytes cannot in principle be avoided, the groove 21 may prove advantageous by virtue of the fact that the air bubbles escaping from the interior 13 of the flow-through cell collect in the groove 21. In a preferred embodiment, this property is in addition provided by chemical treatment of the inner surface of the groove 21 or of the entire inner surface of the flow-through cell, including the groove. This treatment serves to create a hydrophilic, i.e., more readily wettable, surface.

The body 11 preferably is provided with stops 22, 23, and 24, which serve to ensure precise positioning of base plate 31 (see FIGS. 8-15) in relation to the body 11 before the joining together thereof, e.g., by adhesion. There is no mechanical coupling between the stops 22, 23, and 24 and the above-mentioned stops which are used for precise positioning of the body 11 or of the arrangement of flow-through cells formed therewith in the receiving opening 42 of the carrier 41.

The body 11 preferably shows protective angles 25, 26, and 27, which protect base plate 31 from being torn off or from damage which could otherwise occur, especially when the flow-through cell arrangement is inserted in the carrier 41.

In a preferred embodiment, there is a circumferential ridge 29 on the upper part of each flow-through cell, on which a film can be welded. This film not only prevents cross-contamination between the cells; it also prevents fluid losses which could otherwise occur, especially in nucleic acid hybridization assays with process steps at elevated temperatures for example, up to about 80° C.

The following materials are suitable for the manufacture of the body 11:

moldable, sprayable or millable plastics, thermoplastic plastics (preferred manufacture by means of injection molding), metals, silicates, such as glass, quartz or ceramics.

Examples of materials for the manufacture of the body 11 are, in particular:

Polycarbonate (PC), e.g., unfilled, pigmented black

Polybutylene terephthalate (PBT), e.g., filled with glass spheres, pigmented black, and "ABS" (acrylonitrile/butadiene/styrene graft copolymer).

To reduce reflections, it is advantageous if the body 11 of the flow-through cell arrangement is colored black, provided that a light guided in the base plate 31 (when formed as a waveguide) is not to be guided under the walls of body 11 that are in direct contact with the base plate 31.

(2) SECOND EXAMPLE OF A BODY FOR THE FORMATION OF A FLOW-THROUGH CELL ARRANGEMENT

This example is a body according to the invention for the formation of a two-dimensional, matrix-like arrangement of flow-through cells comprising a plurality of rows of cells with the structure of the body 11 described above and containing all the elements described above or elements with an equivalent function. The features of such a body are therefore essentially discernible from FIGS. 1-7.

A body according to this second example is also suitable for forming an arrangement of flow-through cells by joining together with a base plate, which, e.g., carries biological, biochemical or synthetic recognition elements. This body may, for example, already have the outer dimensions and outer features of a standard microtiter plate according to SBS norms.

This body may also have an outer form which fits into a receiving opening of a correspondingly designed carrier (e.g., with outer dimensions according to SBS norms).

Also in this embodiment, the body 11 may be provided with the following elements, which serve to position the body precisely in the receiving opening of the carrier:

(a) a spring and a stop which serve to position the body precisely in the X-direction and are arranged at opposite end sections of the body,
(b) two springs and two matching stops which serve to position the body precisely in the Y-direction and are arranged on opposite sides of the body, wherein the second direction is perpendicular to the first direction,
(c) three points of support and two snap-on hooks, wherein these points of support and snap-on hooks together serve to position the body precisely in the Z-direction.

The same materials which are indicated under (1) can be used for manufacturing the body.

(3) FIRST EXAMPLE OF A FLOW-THROUGH CELL ARRANGEMENT

A first arrangement of flow-through cells according to the invention, comprising a linear row, i.e., a one-dimensional arrangement, of flow-through cells, is shown in FIGS. 8-15. Such an arrangement of flow-through cells is formed by joining together the body 11 described above in relation to FIGS. 1-7 with a base plate 31 which, e.g., carries biological recognition elements. The base plate 31 and body 11 are joined together, for example, by adhesion or by clipping.

In a preferred embodiment, the base plate 31 is suitable for use as a waveguide.

Figure 2:
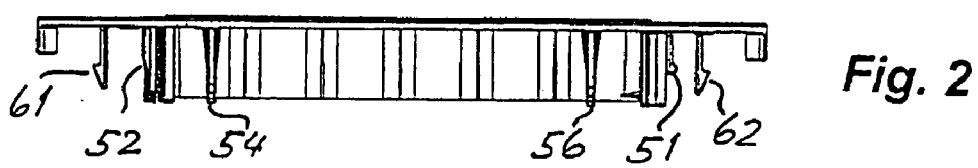
Figure 3:
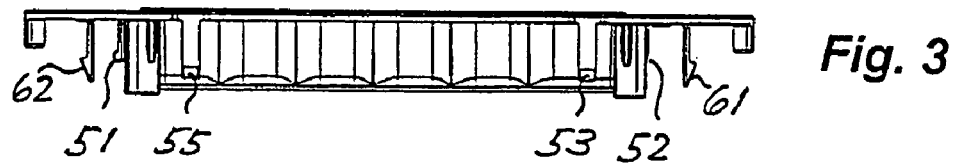
Figure 11:
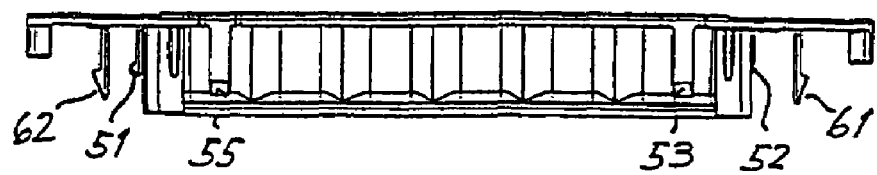
Figure 12:
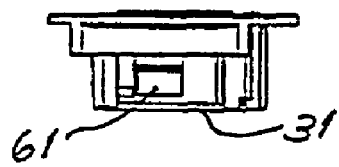
Figure 13:
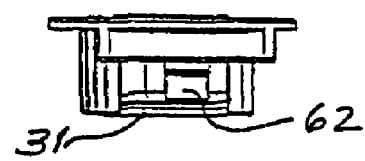
Figure 14:
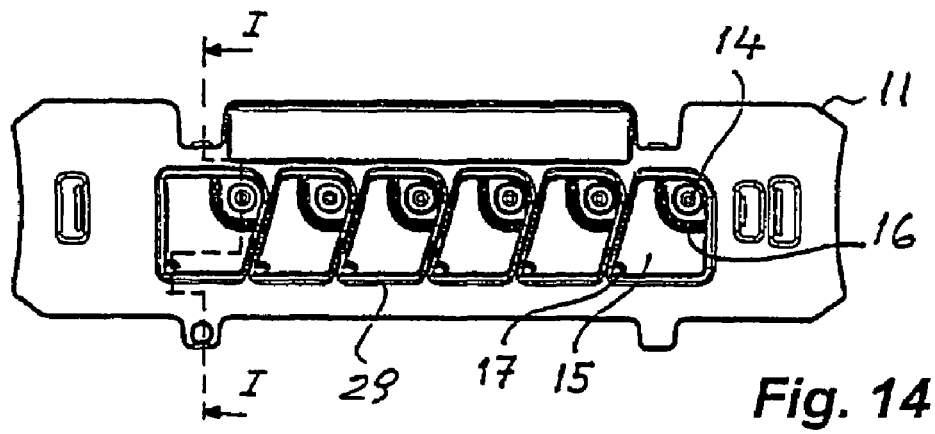
Figure 15:
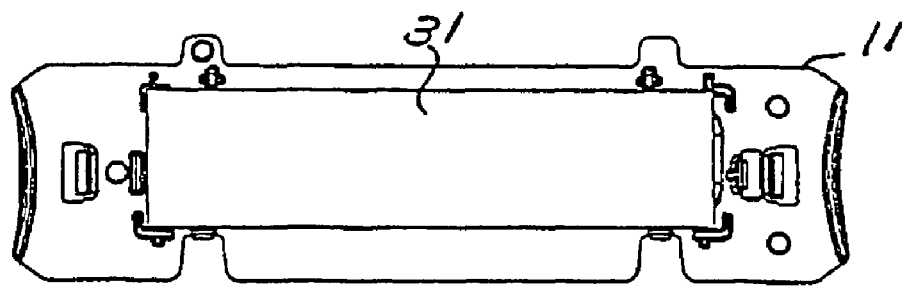
Figure 14A:
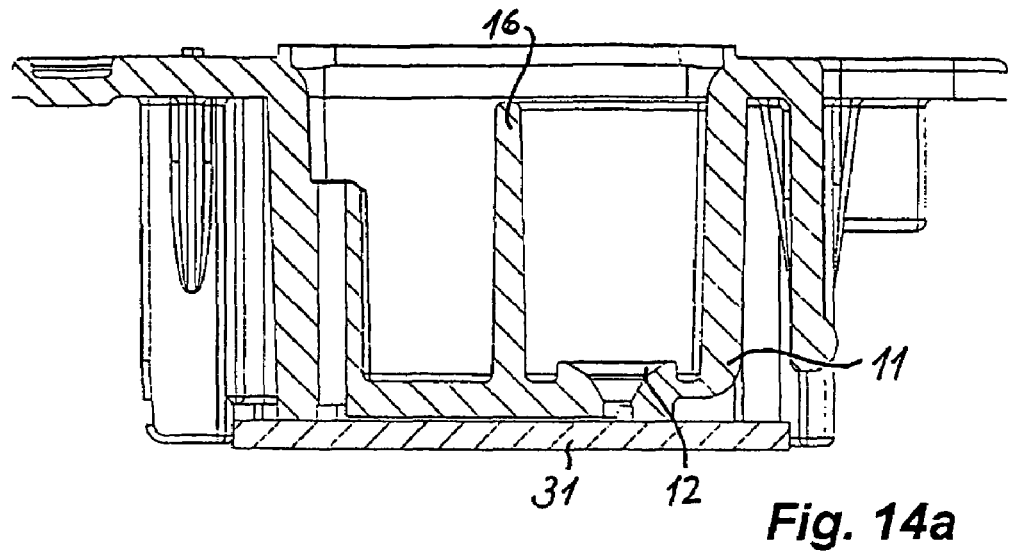
FIG. 14a shows a partial cross-section through plane I-I in FIG. 14.
Figure 14B:
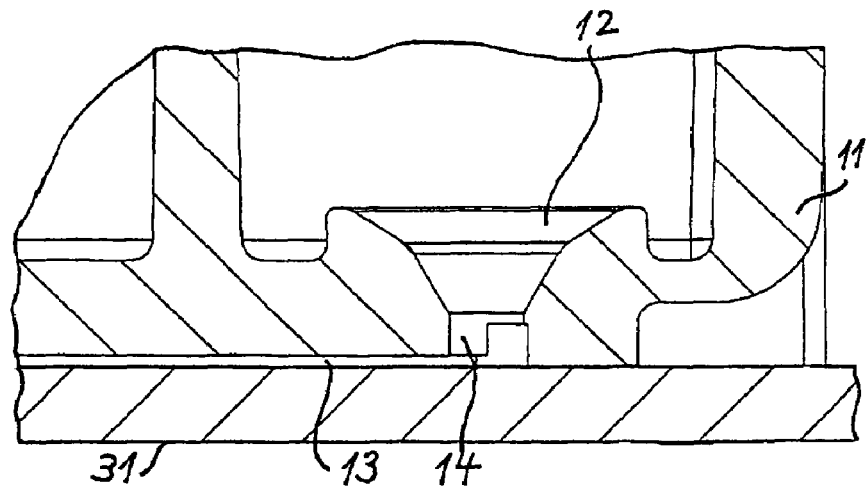
FIG. 14b shows an enlargement of the part encircled in FIG. 14.
Figure 16:
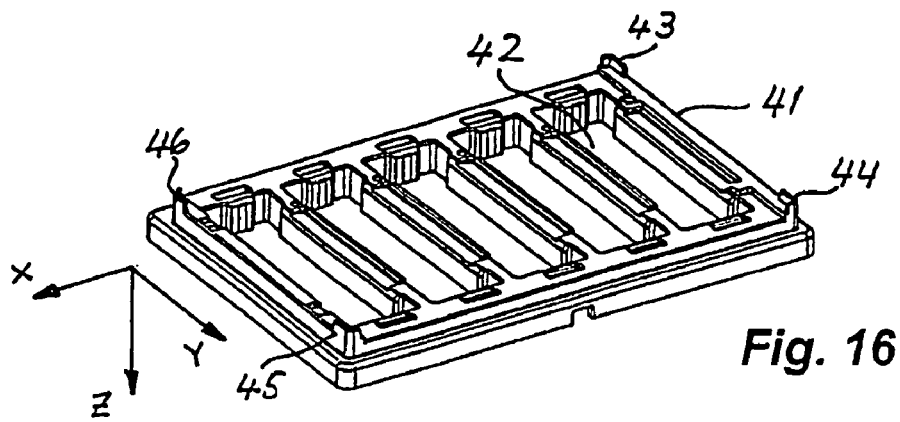
FIGS. 16 to 23 show various views of an embodiment of a carrier according to the invention for accommodating a flow-through cell arrangement or several flow-through cell arrangements according to FIGS. 8-15.
Figure 25:
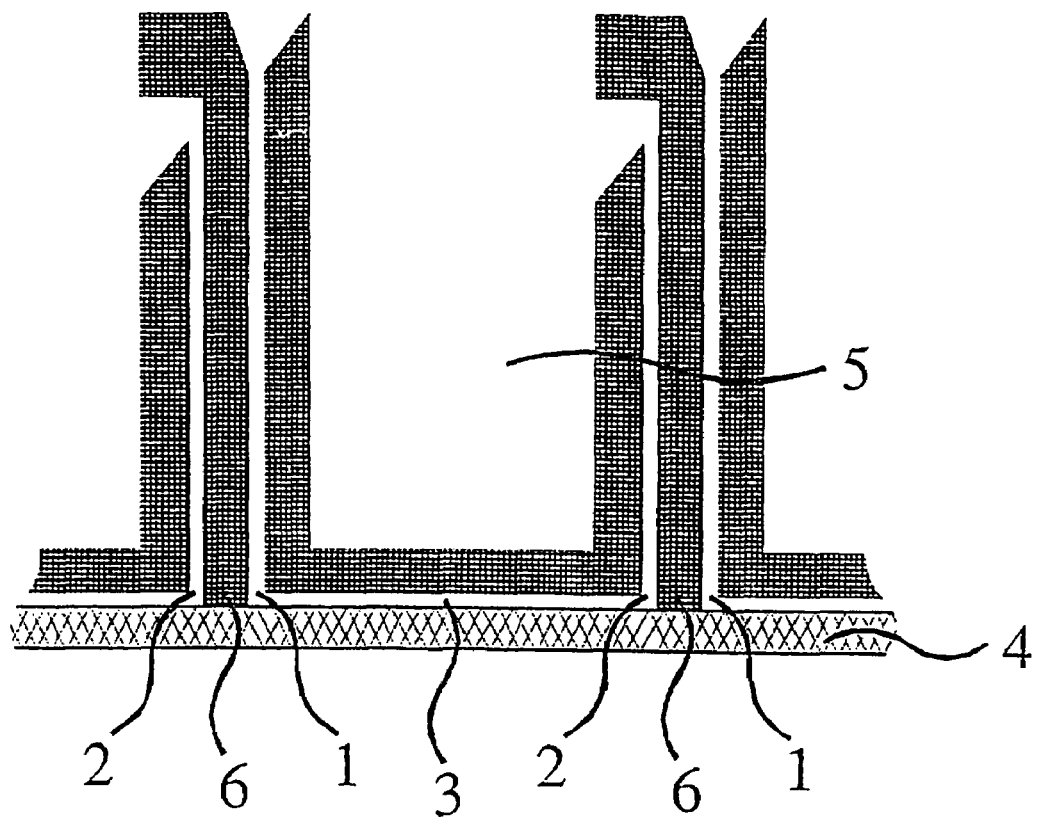
Figure 26:
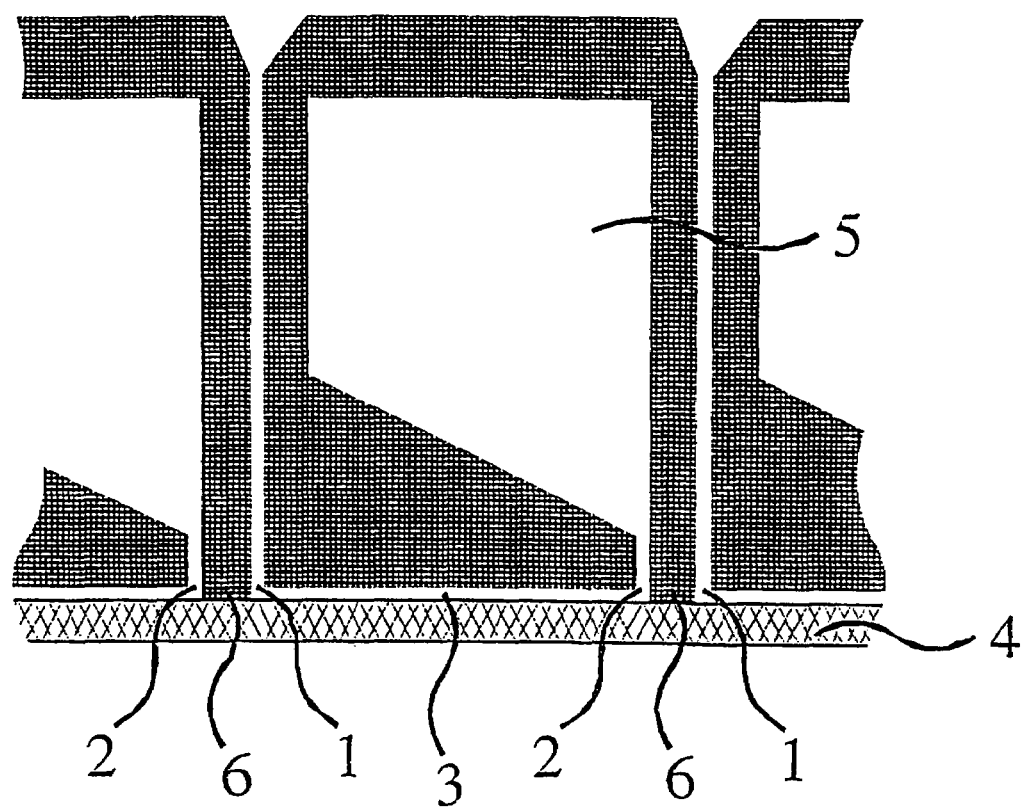

FIGS. 14, 14a and, in particular, FIG. 14b show the following advantageous features of the design of the body 11 according to FIGS. 1-7 and FIGS. 8-15:

Quite unlike in the embodiment shown in FIG. 25 (embodiment according to FIG. 2 of PCT/EP 00/12668), an inlet 12 in the body according to the invention and in the flow-through cell arrangement formed therewith is arranged as an inlet on a low level of the three-dimensional structure of the body 11, and this inlet 12 has only a low, funnel-shaped border, so that, in this embodiment, this outer inlet towards a gap 13 leads to an inner inlet 14 of the flow-through cell without a relatively long channel in between (see FIG. 25, which corresponds to FIG. 2 of PCT/EP 00/12668). This design of the inlet 12 has the following advantages:

(a) The flow-through cells can be filled more easily with pipette tips of larger diameter than in the previous version according to FIG. 25 (embodiment according to FIG. 2 of PCT/EP 00/12668). According to the invention, therefore, especially regular, commercially available tips according to industrial standards can be used.
(b) The required filling volumes or sample volumes for filling can be markedly reduced.

As shown amongst other things in FIG. 6, the body has a limiting wall 16, which serves to separate a reservoir 15 from the inlet opening 14 of each cell and is arranged around this inlet opening.

The materials for the base plate, the body joined thereto and an optionally used additional cover plate must satisfy the requirements for the intended use of the arrangement in each case. Depending on the specific application, these requirements relate to chemical and physical resistance, for example, to acidic or basic media, salts, alcohols or detergents as components of aqueous solutions, or formamide, thermal resistance (e.g., between −30° C. and 100° C.), the most similar possible thermal expansion coefficients of the base plate and the body combined therewith, optical properties (e.g., concerning nonfluorescence and reflectivity), mechanical workability, etc. The material of the body combined with the base plate is preferably selected from the group formed by moldable, sprayable or millable plastics, thermoplastic plastics, metals, and silicates, such as glass, quartz or ceramics. The material of the additional continuous cover plate may likewise be selected from the group which is formed by moldable, sprayable or millable plastics, metals, and silicates, such as glass, quartz or ceramics. Also with regard to the base plate, it is preferred if the material of the base plate comprises materials from the group formed from moldable, sprayable or millable plastics, thermoplastic plastics, metals, and silicates, such as glass, quartz or ceramics. Thereby, the aforementioned components (base plate, the body combined therewith, and the cover plate) may each be composed of a single material or may comprise a mixture of different materials or a composition thereof fitted together in layers or laterally, wherein the materials may substitute each other.

The surfaces of the body 11, which form the "lid" and the side walls of the sample compartments, should show as little reflection as possible, in order to minimize the disturbing influence of excitation light reflected therefrom.

In the proposed mode of use of the arrangement (both for possible refractive measurements and also for fluorescence measurements), the excitation light is generally always radiated through the base plate and the measurement light (at the excitation wavelength and/or at fluorescence or luminescence wavelengths) collected on the same side from which the light irradiation takes place. The material of the base plate is therefore preferably selected such that this is transparent at least at the one or more applied excitation wavelengths used and optionally also at corresponding luminescence wavelengths.

For uses with luminescence detection, the base plate should also be as free as possible from intrinsic luminescence. The base plate may consist of a uniform material (e.g., as glass plate or correspondingly transparent plastic) and be irradiated with excitation light, for example, in a classical epi-illumination configuration. It may also be a multilayer system (formed, for example, as a thin-film waveguide). The light may then also be delivered in the classical configuration just described. The base plate is preferably a (thin-)film waveguide with the properties and embodiments described in PCT/EP 00/12668.

The following materials are, for example, suitable for the manufacture of base plate 31: moldable, sprayable or millable plastics, thermoplastic plastics (preferred manufacture by means of injection molding), metals, silicates, such as glass, quartz or ceramics.

For all applications in which an excitation light is delivered through the base plate 31 in the direction of molecules to be detected thereon, the material of the base plate is selected such that the base plate is largely transparent at least at the wavelength of this excitation light.

Figure 27:
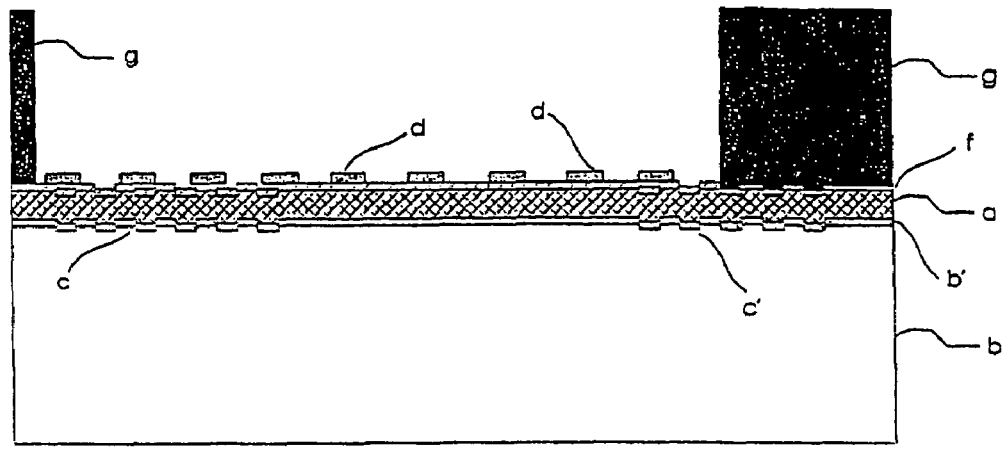
Figure 28:
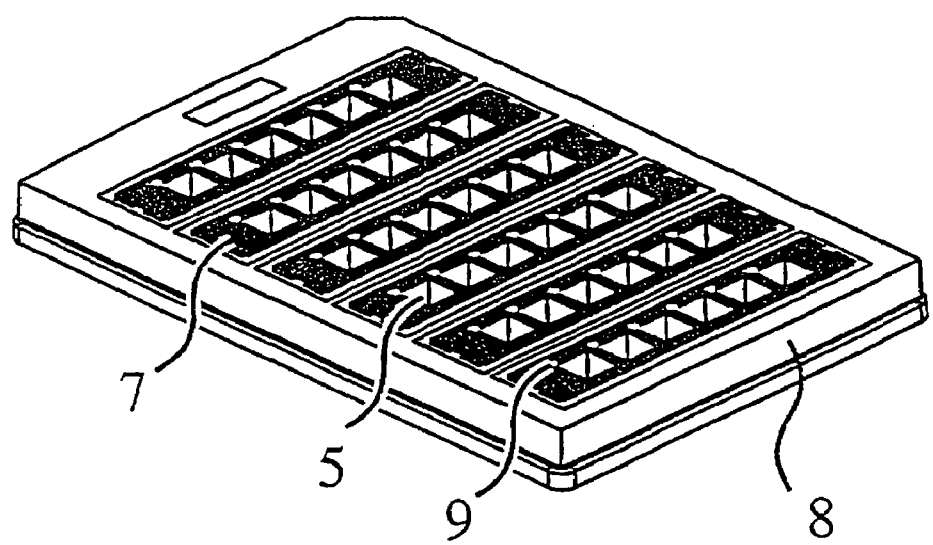

In an embodiment in which the base plate 31 serves as optical film waveguide, the base plate has, for example, the structure indicated in FIG. 27, which shows a cross-section view essentially confined to the base plate. In the embodiment according to FIG. 27, the base plate is provided as an optical film waveguide with biological, biochemical or synthetic recognition elements immobilized thereon. According to FIG. 27, this film waveguide comprises layers a, b and b'. The reference symbol g is used in FIG. 27 to indicate the limitations of a flow-through cell which is created by connecting the base plate with a body. The reference symbol g thus corresponds to reference symbol 11 in FIGS. 1 to 15.

On the layer b which is transparent at least in part of the visible or near-infrared spectrum, the thin intermediate layer b' is first applied and then the layer a, whose refractive index is greater than the refractive indices of the layers b and b'. Also, the layers a and b' are optically transparent at least in part of the visible or near-infrared spectrum. In the layer b, grating structures c and c' are formed as relief gratings, which are transferred to the layers above upon their deposition. On the layer a, an adhesion-promoting layer f is then applied which can improve the adhesion of biological, biochemical or synthetic recognition elements to be immobilized. In this embodiment, these recognition elements are immobilized in spatially separated measurement areas d, which in this embodiment are arranged both on and between the grating structures c and c'. In this embodiment according to FIG. 27, the base plate is finally connected with body g, which corresponds to the body 11 in FIGS. 1 to 15.

The layer a of the base plate is, e.g., a highly refractive metal oxide layer on the layer b.

Examples of materials for the second optically transparent layer b are:

Silicates, e.g., glass or quartz, or a transparent thermoplastic or sprayable plastic, preferably from the group formed by polycarbonate, polyimide, polymethylmethacrylate or polystyrene.

(4) SECOND EXAMPLE OF A FLOW-THROUGH CELL ARRANGEMENT

This second arrangement of flow-through cells according to the invention is formed by joining together a body, which as described in the second example presented above under (2) according to one of the two embodiments of such a body described therein is suitable for forming a matrix-like arrangement of flow-through cells and a base plate which, e.g., carries biological recognition elements. The base plate and body are joined together, for example, by adhesion or by clipping. The flow-through cell arrangement formed in this way can be used in an analysis system either as an independent unit, i.e., without the use of a carrier, or can be used with a carrier which features at least one recess for accommodating the flow-through cell arrangement.

Also in this embodiment, the base plate 31 is preferably suited to use as a waveguide.

The same materials which are indicated above under (3) can be used for manufacturing the components of the flow-through cell arrangement.

(5) FIRST EXAMPLE OF A CARRIER FOR A BODY FOR THE FORMATION OF A FLOW-THROUGH CELL ARRANGEMENT

A carrier 41 for a body 11 according to the invention for the formation of a linear row, i.e., a one-dimensional arrangement, of flow-through cells is presented in FIGS. 16-23. The carrier 41 is provided with multiple recesses 42, the form and dimensions of which are adapted to the outer form of the body 11 in such a way that a precise positioning of the body 11 in the recess 42 is possible.

The outer dimensions of the carrier preferably correspond to the SBS norm. The carrier therefore has the dimensions of a standard microtiter plate, i.e., about 85 mm×128 mm.

The carrier may be designed for single use or as a reusable component from which the flow-through cell arrangements inserted therein can be released by pressing together the snap-on hooks S. Alternatively, the snap-on hooks can also be released by applying pressure from below using a suitably designed tool.

The carrier may accommodate, e.g., up to 5 flow-through cell arrangements comprising, e.g., 6 flow-through cells each.

Figure 17:
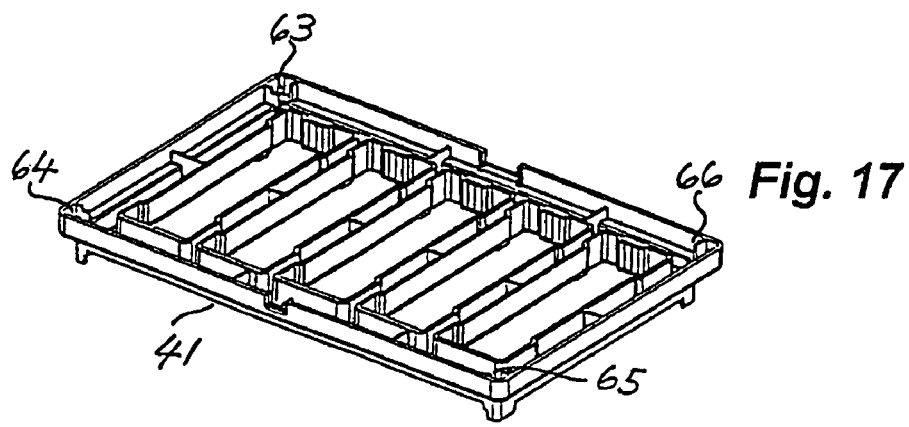
Figure 18:
Figure 19:
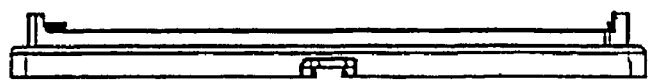
Figure 20:
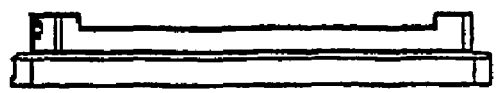
Figure 21:
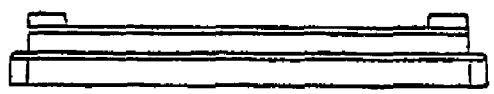
Figure 22:
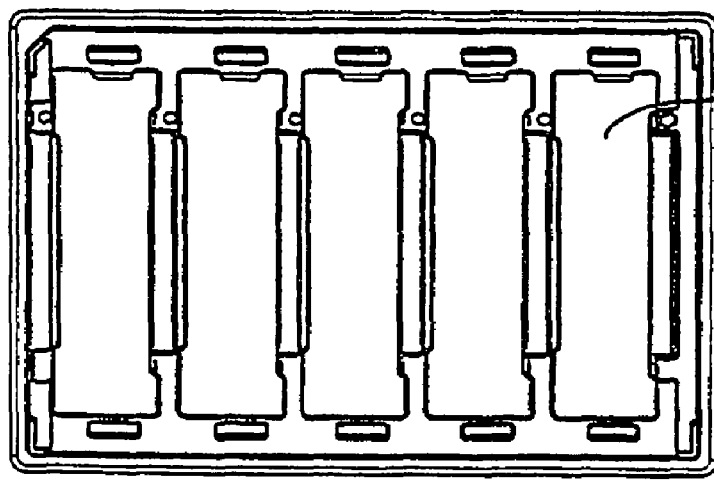
Figure 23:
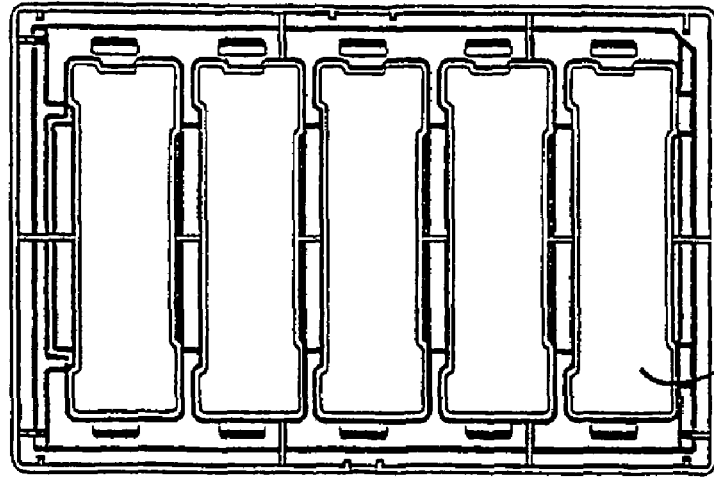
Figure 24:
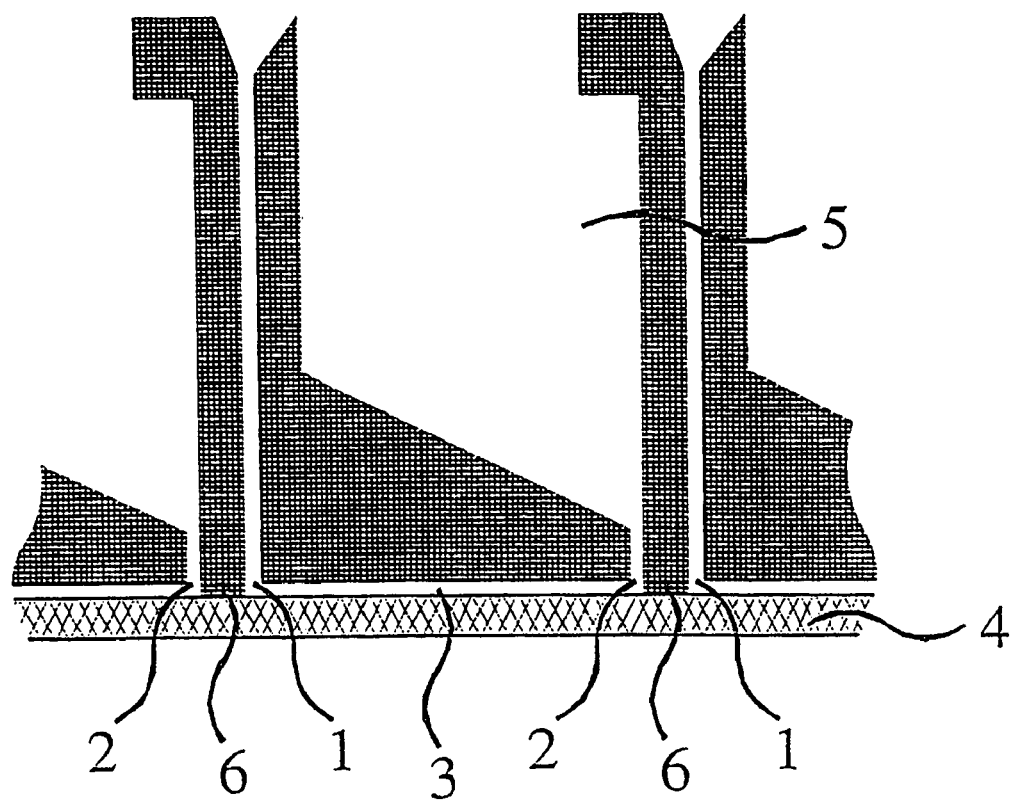
FIGS. 24-28 show embodiments which are described in international patent application PCT/EP 00/12668 and are contained therein as FIGS. 1-5.

On the upper part of the carrier 41 in the outer corners are three identical (square) projections 43, 44, 45 and a further projection 46 that differs from the others (see FIG. 16), which match the recesses 63, 64, 65, 66 on the underside of the carrier 41 (see FIG. 17). These projections and recesses enable several carriers to be stacked on top of each other and at the same time allow the lower parts of the base plates 31 which are to be affixed to the body 11 (glass plates, waveguide plates or sensor platforms) to be held free of contact with the bearing, so that a contamination of the undersides of the base plates is avoided.

On the longitudinal sides of the carrier 41 are two recesses of differing size, which prevent an incorrect insertion of the carrier into the input device of an automated analysis system.

After the insertion of the carrier 41 into the input device, a receiver pin with projections matching the two recesses travels under the carrier in order to lift it slightly. Two light barriers are arranged in parallel to the longitudinal sides of the carrier in the input device. If the carrier is inserted into the input device with an incorrect orientation, the side with the smaller lateral recess is lifted too high. This is detected by a corresponding light barrier, which results in the automatic analysis system refusing to admit the carrier.

The following materials are suitable for the manufacture of the carrier 41:

moldable, sprayable or millable plastics, thermoplastic plastics (preferred manufacture by means of "injection molding"), metals, silicates, such as glass, quartz or ceramics, Examples of materials for the manufacture of the carrier 41 are in particular:

Polycarbonate (PC), e.g., unfilled, pigmented black,

Polybutylene terephthalate (PBT), e.g., filled with glass spheres, pigmented black, Polyphenyl sulfide (PPS), glass/mineral-filled, pigmented black, and "ABS" (acrylonitrile/butadiene/styrene graft copolymer).

To reduce reflections, it is advantageous if the carrier is colored black.

(6) SECOND EXAMPLE OF A CARRIER FOR A BODY FOR THE FORMATION OF A FLOW-THROUGH CELL ARRANGEMENT

This second example of a carrier serves to accommodate at least one body according to (2) above, i.e., a body for the formation of a two-dimensional, matrix-like arrangement of flow-through cells. This second example of a carrier features at least one recess whose form and dimensions are adapted to the outer form of the receiving body in such a way that it allows a precise positioning of the body in the recess.

The same materials which are indicated under (6) can be used for manufacturing the carrier.

(7) FIRST EXAMPLE OF A FLOW-THROUGH CELL ARRANGEMENT SUPPORTED BY A CARRIER

This example of a flow-through cell arrangement comprises one or more flow-through cell arrangements each inserted in an opening 42 of a carrier 41 as shown in FIGS. 16-23, such as that which is described above under (3) with reference to FIGS. 8-15.

The base plate 31 and the body 11 are joined together, for example, by adhesion. As an alternative variant, the base plate 31 is inserted between the body 11 and the carrier 41 and joined to the body solely by means of a force which is generated by the combination of the body 11 and the carrier 41.

In this variant, the base plate is held in place as follows:

On the underside of the carrier 41 are thin (e.g., 0.3 mm thick) supporting ridges running around the receiving openings, so that the base plates 31 (e.g., glass plates, waveguide plates, sensor platforms) featuring (on the upper part) biological, biochemical or synthetic recognition elements can first be inserted into the carrier 41. Only then are the bodies 11, with integrated sealing lips or O-rings (e.g., made of elastic plastic), which may contain the grooves 21 shown in FIG. 7, inserted into the carrier 41 with, e.g., barb-like holders in such a way that a contact pressure of defined strength is generated between the bodies 11 and the base plate 31 such as to create a reciprocal fluidic seal of the flow-through cell created together with the base plate 31.

For this variant, suitable bodies 11, comprising rigid and elastic plastic parts, are preferably manufactured using a two-component injection molding process. Alternatively, this variant may comprise a correspondingly designed rigid plastic body and sealing rings to be inserted into matching recesses of the body. Such an embodiment also especially enables the immobilization of biological, biochemical or synthetic recognition elements to be carried out in situ by the customer (for example, by "spotting") on the base plates 31.

For the manufacture of the body 11 by a two-component injection molding process, the (plastic) materials for the rigid components are as mentioned hereinbefore. For the second elastic component, which is joined with the based plate in a tight seal, preferred materials are: thermoelastic plastics (TPE), e.g., styrene-ethylene-butadiene-styrene (SEBS), silicon, and elastomers (rubber).

(8) SECOND EXAMPLE OF A FLOW-THROUGH CELL ARRANGEMENT SUPPORTED BY A CARRIER

This example of a flow-through cell arrangement comprises at least one flow-through cell arrangement inserted into an opening of a carrier according to (6) above, such as that described above under (4).

Alternatively, the flow-through cell arrangement may be formed in such a manner that it forms an independent unit which does not need any carrier in order to be used in an analysis system.

Such a flow-through cell arrangement may, e.g., comprise 96 flow-through cells or more, e.g., 384 or 1536 flow-through cells which are arranged on the same footprint, or also arrays with any dimensions.

The base plate and body are joined together, for example, by adhesion or by clipping. As an alternative, the base plate is inserted in one variant between the body according to a variant described in example 7 and the carrier, and joined to the body solely by means of a force which is generated by the combination of the body and the carrier.

(9) EXAMPLES OF PROCESSES WHICH CAN BE PERFORMED USING THE FLOW-THROUGH CELL ARRANGEMENTS DESCRIBED ABOVE

For the sake of simplicity, the following paragraphs from 1 to 18 are numbered and phrases of the type "A process according to N1-N2" are used, wherein this is understood to mean "A process according to paragraphs N1 to N2".

The following processes, amongst others, can be carried out using the flow-through cell arrangements described hereinabove:

(9.1) A process for detection of one or more analytes in one or more liquid samples using a flow-through cell arrangement, wherein sample liquids and optionally further reagent liquids are added to the sample compartments and may exit into a reservoir, as a part of the sample compartments, which is fluidically connected to a flow-through cell.

(9.2) A process according to (9.1), wherein biological, biochemical or synthetic recognition elements for the detection of one or more analytes are immobilized on the base plate of the configuration, excitation light is delivered to the measurement areas on the base plate and the light emanating from the measurement areas is determined using at least one detector.

(9.3) A process according to (9.2), wherein the base plate comprises an optical waveguide which is continuous or divided up into separate areas, excitation light is delivered via an optical coupling element into the optical waveguide, and measurement light from the measurement areas is determined using one or more detectors which are in optical interaction with the optical waveguide.

(9.4) A process according to (9.3), wherein the optical waveguide is provided as an optical film waveguide with a first optically transparent layer a on a second optically transparent layer b with lower refractive index than layer a, wherein, further on, excitation light is in-coupled into the optically transparent layer a by means of one or more grating structures provided in the optically transparent layer a and is delivered as a guided wave to the measurement areas d located thereon, and wherein the luminescence of molecules capable of luminescence, generated in the evanescent field of the guided wave, is further determined using one or more detectors, and the concentration of one or more analytes is determined from the intensity of these luminescence signals.

(9.5) A process according to (9.4), wherein (1) the isotropically emitted luminescence or (2) luminescence in-coupled into the optically transparent layer a and out-coupled via grating structure c or luminescences of both parts (1) and (2) are measured simultaneously.

(9.6) A process according to (9.4)-(9.5) wherein, for the generation of luminescence, a luminescent dye or a luminescent nanoparticle is used as a luminescence label, which can be excited and emits at a wavelength between 300 nm and 1100 nm.

(9.7) A process according to (9.6), wherein the luminescence label is bound to the analyte or, in a competitive assay, to an analogue of the analyte or, in a multistep assay, to one of the binding partners of the immobilized biological, biochemical or synthetic recognition elements or to the biological, biochemical or synthetic recognition elements.

(9.8) A process according to (9.6)-(9.7), wherein a second luminescence label or further luminescence labels are used with the same or different excitation wavelengths as the first luminescence label and with the same or different emission wavelengths.

(9.9) A process according to (9.8), wherein the second or further luminescence labels can be excited at the same wavelength as the first luminescent dye, but emit at different wavelengths.

(9.10) A process according to (9.8), wherein the excitation spectra and emission spectra of the luminescent dyes used overlap only little or not at all.

(9.11) A process according to (9.8), wherein charge or optical energy transfer from a first luminescent dye serving as a donor to a second luminescent dye serving as an acceptor is used for the purpose of detecting the analyte.

(9.12) A process according to (9.4)-(9.11) wherein, in addition to the determination of one or more luminescences, changes in the effective refractive index on the measurement areas are determined.

(9.13) A process according to (9.4)-(9.12), wherein the one or more luminescences and/or determinations of light signals at the excitation wavelength are carried out in a polarization-selective way.

(9.14) A process according to (9.4)-(9.13), wherein the one or more luminescences are measured at a polarization different from that of the excitation light.

(9.15) A process according to (9.4)-(9.14) for simultaneous or sequential, quantitative or qualitative determination of one or more analytes from the group of antibodies or antigens, receptors or ligands, chelators or "histidine tag components", oligonucleotides, DNA or RNA strands, DNA or RNA analogs, enzymes, enzyme cofactors or inhibitors, lectins and carbohydrates.

(9.16) A process according to (9.4)-(9.15), wherein the samples to be tested are naturally occurring body fluids, such as blood, serum, plasma, lymph or urine, tissue fluids or egg yolk.

(9.17) A process according to (9.4)-(9.15), wherein the sample to be tested is an optically turbid fluid, a surface water, a soil or plant extract, or a biological or synthetic process broth.

(9.18) A process according to (9.4)-(9.17), wherein the samples to be tested are taken from biological tissue parts.

(10) EXAMPLES OF APPLICATIONS OF THE ABOVE-DESCRIBED ARRANGEMENTS AND PROCESSES

The bodies, carriers, arrangements of flow-through cells and processes described hereinabove are suitable for the following applications:

Applications for quantitative or qualitative analyses for the determination of chemical, biochemical or biological analytes in screening methods in pharmaceutical research, combinatorial chemistry, clinical and preclinical development, for real-time binding studies and for the determination of kinetic parameters in affinity screening and in research, for qualitative and quantitative analyte determinations, especially for DNA and RNA analysis and the determination of genomic and proteomic differences in the genome, such as single nucleotide polymorphisms, for the measurement of DNA-protein interactions, for the determination of control mechanisms for mRNA expression and for protein (bio)synthesis, for the generation of toxicity studies and for the determination of expression profiles, in particular for the determination of biological and chemical marker substances, such as mRNA, proteins, peptides or low-molecular organic (messenger) substances, and for the determination of antibodies, antigens, pathogens or bacteria in pharmaceutical product research and development, human and veterinary diagnostics, agrochemical product research and development, for symptomatic and presymptomatic plant diagnostics, for patient stratification in pharmaceutical product development and for therapeutic drug selection, and/or for the determination of pathogens and noxious substances, in particular salmonellae, prions, viruses and bacteria, especially in food and environmental analysis.

8. LIST OF REFERENCE SYMBOLS a Layer
b Layer
b' Intermediate layer
c Grating structure
c' Grating structure
d Measurement area
f Adhesion-promoting layer
g Limitation of flow-through cell (corresponds to reference symbol 6)
1 Inlet
2 Outlet
3 Recess
4 Base plate
5 Reservoir
6 Body
7 Flow-through cell arrangement (application block)
8 Carrier ("meta-carrier")
9 Inlet openings
10
11 Body
12 Inlet
13 Gap
14 Inlet opening of gap 13
15 Reservoir
16 Limiting wall
17 Outlet opening of gap 13
18 Position of a flow-through cell
19
20
21 Groove (circumferential groove)
22 Stop
23 Stop
24 Stop
25 Protective angle
26 Protective angle
27 Protective angle
28
29 Ridge (circumferential ridge)
30
31 Base plate
32
33
34
35
36
37
38
39
40
41 Carrier
42 Recess/receiving opening
43 Projection
44 Projection
45 Projection
46 Projection
57
48
49
50
51 Spring
52 Stop
53 Spring
54 Stop
55 Spring
56 Stop
57 Point of support
58 Point of support
59 Point of support
60
61 Snap-on hook
62 Snap-on hook
63 Recess
64 Recess 65 Recess
66 Recess
67
68
69
70
71
72
73
74
75
76
77
78
79

What is claimed is:

1. An arrangement comprising:
a body having a three-dimensional structure; and
a base plate joined to the body,
wherein the body comprises a reservoir, a limiting wall and at least one flow-through cell part having an inlet and an outlet,
wherein the limiting wall separates the reservoir from the inlet and forms a channel above the inlet and the limiting wall has a height lower than the height of the body,
the outlet is located in the reservoir,
wherein an interior space is formed between the body and the base plate, the interior space having an inlet opening and an outlet opening, and fluidically connecting the inlet and the outlet,
wherein the at least one flow-through part and the interior space form a flow-through cell, and
wherein the inlet is arranged on the three-dimensional structure of the body closer to the base plate than an opening of the channel away from the inlet and the inlet has a funnel-shaped border and is adapted to discharge to the inlet opening towards the base plate, the funnel-shaped border having a shape allowing a tip of a pipette to be maneuvered close to the base plate to fill the flow-through cell.

2. The arrangement according to claim 1, wherein the flow-through cell part has an area forming a part of the interior space and at least one groove, wherein the inlet opening and the outlet opening are located in the at least one groove.

3. The arrangement according to claim 1, wherein the body has an outer shape adapted to fit into a receiving opening of a carrier.

4. The arrangement according to claim 3, wherein the body further comprises a plurality of the flow-through cells each having an inlet and an outlet.

5. The arrangement according to claim 4, wherein the base plate carries at least one of biological recognition elements, biochemical recognition elements and synthetic recognition elements.

6. The arrangement according to claim 4, wherein the base plate is a waveguide.

7. A carrier for accommodating the arrangement according to claim 4, the carrier comprising the receiving opening having a shape and dimensions adapted to the outer shape of the body such that the receiving opening allows a precise positioning of the body in the receiving opening.

8. The carrier according to claim 7, wherein the carrier comprises a plurality of the receiving openings.

9. A second arrangement comprising the arrangement according to claim 4 and the carrier comprising the receiving opening having a shape and dimensions adapted to the outer shape of the body such that the receiving opening allows a precise positioning of the body in the receiving opening.

10. The second arrangement according to claim 9, wherein the carrier comprises a plurality of the receiving openings.

11. The arrangement according to claim 1, wherein the inlet has a first funnel-shaped portion and a second funnel-shaped portion, the second funnel-shaped portion being closer to the base plate than the first funnel-shaped portion, and the second funnel-shaped portion has an angle of incline that is less than 90°.

12. A method comprising determining one or more analytes in a sample liquid with the carrier according to claim 7.

13. A method comprising performing at least one of:
(a) quantitative analysis or qualitative analysis for determination of chemical, biochemical or biological analytes in screening methods in pharmaceutical research, combinatorial chemistry, clinical and preclinical development,
(b) real-time binding studies and determining kinetic parameters in affinity screening and research,
(c) qualitative and quantitative analyte determinations,
(d) measurement of DNA-protein interactions,
(e) determination of control mechanisms for mRNA expression and for protein synthesis,
(f) generation of toxicity studies,
(g) determination of expression profiles,
(h) determination of antibodies, antigens, pathogens or bacteria in pharmaceutical product research and development, human and veterinary diagnostics, agrochemical product research and development, for symptomatic and presymptomatic plant diagnostics,
(i) patient stratification in pharmaceutical product development and for therapeutic drug selection, and
(j) determination of pathogens and noxious substances,
with the carrier according to claim 7.

14. A method comprising determining one or more analytes in a sample liquid with the second arrangement according to claim 9.

15. A method comprising performing at least one of:
(a) quantitative analysis or qualitative analysis for determination of chemical, biochemical or biological analytes in screening methods in pharmaceutical research, combinatorial chemistry, clinical and preclinical development,
(b) real-time binding studies and determining kinetic parameters in affinity screening and research,
(c) qualitative and quantitative analyte determinations,
(d) measurement of DNA-protein interactions,
(e) determination of control mechanisms for mRNA expression and for protein synthesis,
(f) generation of toxicity studies,
(g) determination of expression profiles,
(h) determination of antibodies, antigens, pathogens or bacteria in pharmaceutical product research and development, human and veterinary diagnostics, agrochemical product research and development, for symptomatic and presymptomatic plant diagnostics,
(i) patient stratification in pharmaceutical product development and for therapeutic drug selection, and
(j) determination of pathogens and noxious substances,
with the second arrangement according to claim 9.

16. A method comprising determining one or more analytes in a sample liquid with the arrangement according to claim 4.

17. A method comprising performing at least one of:
  (a) quantitative analysis or qualitative analysis for determination of chemical, biochemical or biological analytes in screening methods in pharmaceutical research, combinatorial chemistry, clinical and preclinical development,
  (b) real-time binding studies and determining of kinetic parameters in affinity screening and research,
  (c) qualitative and quantitative analyte determinations,
  (d) measurement of DNA-protein interactions,
  (e) determination of control mechanisms for mRNA expression and for protein synthesis,
  (f) generation of toxicity studies,
  (g) determination of expression profiles,
  (h) determination of antibodies, antigens, pathogens or bacteria in pharmaceutical product research and development, human and veterinary diagnostics, agrochemical product research and development, for symptomatic and presymptomatic plant diagnostics,
  (i) patient stratification in pharmaceutical product development and for therapeutic drug selection, and
  (j) determination of pathogens and noxious substances,
  with the arrangement according to claim 4.

18. A method comprising determining one or more analytes in a sample liquid with the arrangement according to claim 1.

19. A method comprising determining at least one of:
  (a) quantitative analysis or qualitative analysis for determination of chemical, biochemical or biological analytes in screening methods in pharmaceutical research, combinatorial chemistry, clinical and preclinical development,
  (b) real-time binding studies and determining kinetic parameters in affinity screening and research,
  (c) qualitative and quantitative analyte determinations,
  (d) measurement of DNA-protein interactions,
  (e) determination of control mechanisms for mRNA expression and for protein synthesis,
  (f) generation of toxicity studies,
  (g) determination of expression profiles,
  (h) determination of antibodies, antigens, pathogens or bacteria in pharmaceutical product research and development, human and veterinary diagnostics, agrochemical product research and development, for symptomatic and presymptomatic plant diagnostics,
  (i) patient stratification in pharmaceutical product development and for therapeutic drug selection, and
  (j) determination of pathogens and noxious substances,
  with the arrangement according to claim 1.

* * * * *